United States Patent
Kanda (10) Patent No.: US 10,730,052 B2
(45) Date of Patent: Aug. 4, 2020

(54) APPARATUS FOR FORMING LIQUID FLOW INCLUDING BIOLOGICAL PARTICLES, AND TREATMENT APPARATUS

(71) Applicant: Allied Flow Inc., Nishinomiya-shi (JP)

(72) Inventor: Masahiko Kanda, Nishinomiya-Hyogo (JP)

(73) Assignee: Allied Flow, Inc., Hyogo (JP)

( * ) Notice: Subject to any disclaimer, the term of this patent is extended or adjusted under 35 U.S.C. 154(b) by 92 days.

(21) Appl. No.: 16/098,141

(22) PCT Filed: May 1, 2017

(86) PCT No.: PCT/JP2017/017120
§ 371 (c)(1),
(2) Date: Nov. 1, 2018

(87) PCT Pub. No.: WO2017/191824
PCT Pub. Date: Nov. 9, 2017

(65) Prior Publication Data
US 2019/0143330 A1    May 16, 2019

(30) Foreign Application Priority Data
May 6, 2016 (JP) ................................ 2016-093358

(51) Int. Cl.
*C12N 13/00* (2006.01)
*G01N 15/14* (2006.01)
(Continued)

(52) U.S. Cl.
CPC ................. *B01L 3/52* (2013.01); *B01L 3/502* (2013.01); *C12M 47/04* (2013.01);
(Continued)

(58) Field of Classification Search
CPC .... B01L 3/52; B01L 3/502; B01L 2300/0645; B01L 2300/0609; B01L 2300/0627;
(Continued)

(56) References Cited

U.S. PATENT DOCUMENTS 6,248,590 B1    6/2001 Malachowski
2001/0033380 A1*  10/2001 Colon ................ G01N 15/1404
356/436

(Continued)

FOREIGN PATENT DOCUMENTS

JP          06288896        10/1994
JP          2002-505423      2/2002
(Continued)

OTHER PUBLICATIONS

Office Action issued in Japanese Patent Application No. 2016-093358, dated Feb. 25, 2020, English translation attached.

*Primary Examiner* — Huy Tram Nguyen
(74) *Attorney, Agent, or Firm* — Barnes & Thornburg LLP; Jeffrey R. Stone (57) ABSTRACT

There are provided an apparatus capable of treating biological particles in a sterile state, and a treatment apparatus. An apparatus for forming a liquid flow including biological particles includes: a chamber member; a sample liquid supply portion; a sheath liquid supply portion; and a vibrating electrode member. The chamber member includes a chamber and a flow cell extending from an interior to an exterior of the chamber. The sample liquid supply portion is configured to supply a sample liquid including the biological particles into the chamber. The sheath liquid supply portion is configured to supply a sheath liquid into the chamber. The vibrating electrode member extends from the interior to the exterior of the chamber, is made of an electrically conductive material, and is configured to be capable of supplying an (Continued)

electric charge to the sheath liquid and the sample liquid in the chamber and propagating an ultrasonic vibration.

7 Claims, 4 Drawing Sheets

(51) Int. Cl.
  *B01L 3/00* (2006.01)
  *C12M 1/00* (2006.01)
  *G01N 15/10* (2006.01)
(52) U.S. Cl.
  CPC ..... *G01N 15/1404* (2013.01); *G01N 15/1459* (2013.01); *B01L 2300/0609* (2013.01); *B01L 2300/0627* (2013.01); *B01L 2300/0645* (2013.01); *B01L 2400/0439* (2013.01); *G01N 2015/1006* (2013.01); *G01N 2015/142* (2013.01); *G01N 2015/149* (2013.01); *G01N 2015/1422* (2013.01)
(58) Field of Classification Search
  CPC ........ B01L 2400/0439; G01N 15/1459; G01N 15/1404; G01N 2015/149; G01N 2015/1006; G01N 2015/142; G01N 2015/1422; C12M 47/04
  USPC .......................................................... 422/128
  See application file for complete search history.

(56) References Cited

U.S. PATENT DOCUMENTS

| 2009/0308473 | A1 | 12/2009 | Shinoda |
| 2010/0178682 | A1* | 7/2010 | Nakada ................ G01N 15/147 435/173.9 |
| 2010/0297759 | A1 | 11/2010 | Kanda |
| 2011/0259749 | A1 | 10/2011 | Kanda |
| 2011/0284378 | A1 | 11/2011 | Shinoda |
| 2014/0170697 | A1 | 6/2014 | Sharpe et al. |
| 2015/0285726 | A1 | 10/2015 | Tanase et al. |
| 2017/0010203 | A1 | 1/2017 | Otsuka et al. |
| 2017/0227446 | A1 | 8/2017 | Tabata et al. |

FOREIGN PATENT DOCUMENTS

| JP | 2010025911 | 2/2010 |
| JP | 2011232033 | 11/2011 |
| JP | 2014095595 | 5/2014 |
| JP | 2015152439 | 8/2015 |
| WO | 1999/44037 | 9/1999 |
| WO | 2008/153056 | 12/2008 |
| WO | 2009/078307 | 6/2009 |
| WO | 2010/095391 | 8/2010 |
| WO | 2016/031486 | 3/2016 |

* cited by examiner

APPARATUS FOR FORMING LIQUID FLOW INCLUDING BIOLOGICAL PARTICLES, AND TREATMENT APPARATUS

TECHNICAL FIELD

The present invention relates to an apparatus for forming a liquid flow including biological particles, and a treatment apparatus. More particularly, the present invention relates to an apparatus for performing treatment such as analysis and separation of biological particles in a sterile state, and a treatment apparatus.

BACKGROUND ART

With the development of biotechnology, a demand for an apparatus for performing treatment such as sorting and analysis of multiple cell particles, which are one example of biological particles, has been increasing in various fields including medicine and biology. One example of such an apparatus is a flow cytometer or a cell sorter (refer to, for example, Japanese Patent Laying-Open No. 2011-232033).

CITATION LIST

Patent Document

PTD 1: Japanese Patent Laying-Open No. 2011-232033

SUMMARY OF INVENTION

Technical Problem

When the above-described apparatus is applied to, for example, regenerative medicine, antibody medicine or the like, it is desirable to treat cell particles in a sterile state. Therefore, it is conceivable, for example, to dispose the above-described apparatus in a safety cabinet placed in a room of level 1 of a cell processing center (CPC), and perform sorting, analysis and the like of cell particles. However, even when the cell particles are treated using such an apparatus, an aerosol generated during treatment of the cell particles contaminates an interior of the apparatus. Therefore, in order to perform the above-described treatment in a sterile state when the cell particles are treated and then another cell particles are treated, it is necessary to remove such contamination by the aerosol from the interior of the apparatus. Conventionally, however, contamination by the aerosol has not been effectively removed.

The present invention has been made to solve the above-described problem, and an object of the present invention is to provide an apparatus capable of treating biological particles in a sterile state, and a treatment apparatus.

Solution to Problem

An apparatus according to the present invention is an apparatus for forming a liquid flow including biological particles, the apparatus including: a chamber member; a sample liquid supply portion; a sheath liquid supply portion; and a vibrating electrode member. The chamber member includes a chamber and a flow cell extending from an interior to an exterior of the chamber. The sample liquid supply portion is configured to supply a sample liquid including the biological particles into the chamber. The sheath liquid supply portion is configured to supply a sheath liquid into the chamber. The vibrating electrode member extends from the interior to the exterior of the chamber, is made of an electrically conductive material, and is configured to be capable of supplying an electric charge to the sheath liquid and the sample liquid in the chamber and propagating an ultrasonic vibration.

A treatment apparatus according to the present invention includes: a sterilization treatment portion; and the above-described apparatus. The sterilization treatment portion includes a sterilization treatment possible region where sterilization treatment is possible. The above-described apparatus is disposed in the sterilization treatment possible region.

Advantageous Effects of Invention

According to the present invention, in an apparatus for forming a liquid flow including biological particles, contamination by an aerosol of the liquid flow can be prevented, and thus, the biological particles can be treated in a sterile state.

DESCRIPTION OF EMBODIMENTS

An embodiment of the present invention will be described hereinafter with reference to the drawings. In the following drawings, the same or corresponding portions are denoted by the same reference numerals and description thereof will not be repeated.

<Configuration of Treatment Apparatus>

A treatment apparatus according to the present embodiment will be described with reference to FIGS. 1 to 4. The treatment apparatus shown in FIGS. 1 to 4 is an apparatus for treating biological particles. Hereinafter, in order to facilitate understanding of the present invention, a cell sorter functioning as the treatment apparatus will be described by way of example. However, the present invention is also applicable to a flow cytometer.

The cell sorter functioning as the treatment apparatus according to the present embodiment is an apparatus described below. Specifically, the apparatus is configured to selectively apply an electric charge to liquid droplets including individual cell particles jetted from a flow cell, based on unique identification information such as scattered light from cell particles, which are one example of biological particles, and fluorescence, and then, form a DC electric field on a path onto which the droplets drop, and sort out a course of the droplets, thereby fractionating and sorting a particular cell particle.

A flow cytometer functioning as the treatment apparatus according to the present embodiment is an apparatus described below. Specifically, the apparatus is configured to color multiple cell particles taken from, for example, blood or the like of a living body with a fluorescent labeling reagent or the like, and then, form a sheath flow in which a sample liquid including the cell particles is surrounded by a sheath liquid, and then, introduce this sheath flow into a flow cell and apply, for example, a laser beam to each of the cell particles arranged in line in the flow cell, and then, measure scattered light such as forward scattered light and side scattered light from the cell particles and multicolor fluorescence dependent on the fluorescent labeling reagent, and analyze the cell particles based on a result of this measurement.

The treatment apparatus shown in FIGS. 1 to 4 is a cell sorter 1 and includes a sterilization treatment portion 10, a sort head 81 functioning as the apparatus according to the present embodiment, an ultrasonic vibration generation portion 31, an optical mechanism 61, a controller 71, a sample liquid source portion 26, and a sheath liquid source portion 27. Sterilization treatment portion 10 is, for example, an isolator and includes a sterilization treatment possible region 12 where sterilization treatment is possible, and a diaphragm 11. Diaphragm 11 has an opening 14 and partitions an exterior of sterilization treatment possible region 12 (non-sterilization treatment region 13) and sterilization treatment possible region 12. Sort head 81 described above is disposed in sterilization treatment possible region 12. In cell sorter 1, an interior of sterilization treatment possible region 12 is kept in an airtight state. The interior of sterilization treatment possible region 12 is also kept in a sterile state.

Ultrasonic vibration generation portion 31, optical mechanism 61 and controller 71 are disposed in non-sterilization treatment region 13 of sterilization treatment portion 10. Sample liquid source portion 26 and sheath liquid source portion 27 are disposed outside sterilization treatment portion 10.

(Sort Head)

Sort head 81 functioning as the apparatus according to the present embodiment is an apparatus for forming a liquid flow including cell particles, which are one example of biological particles, and includes a flow cell chamber unit 80 and a sorter mechanism portion 40.

(Flow Cell Chamber Unit)

Flow cell chamber unit 80 includes a chamber member 28, a sample liquid supply portion 24, a sheath liquid supply portion 25, a vibrating electrode member 35, deflection plates 41 and 42, and a collection member 43. Chamber member 28 includes a sheath and sample mixing chamber 21 (hereinafter also simply referred to as "chamber 21") functioning as a chamber, and a flow cell 22 extending from an interior to an exterior of chamber 21. Flow cell 22 is connected to a lower part of chamber 21. Sample liquid supply portion 24 supplies a sample liquid including the biological particles into chamber 21. A conduit 23 (also referred to as "sample tube") is disposed so as to extend from sample liquid supply portion 24 to the interior of chamber 21. Sample liquid supply portion 24 is disposed above chamber 21. Conduit 23 is disposed so as to extend from the upper part to the lower part of chamber 21. Sample liquid source portion 26 is connected to sample liquid supply portion 24 through a pipe.

Sheath liquid supply portion 25 supplies a sheath liquid into chamber 21. Sheath liquid supply portion 25 is disposed on a side part of chamber 21. Sheath liquid source portion 27 is connected to sheath liquid supply portion 25 through a pipe. Vibrating electrode member 35 extends from the interior to the exterior of chamber 21 and is made of an electrically conductive material. Vibrating electrode member 35 is connected to chamber 21 from the side part of chamber 21. That is, an end face of vibrating electrode member 35 exposed to the interior of chamber 21 is exposed to the interior of chamber 21 through an opening formed in a side surface portion on an inner circumferential surface of chamber 21. The end face of vibrating electrode member 35 is disposed so as to be continuous with a portion of an inner surface of chamber 21 adjacent to the end face.

An electrically conductive member 36 is connected to vibrating electrode member 35. Stainless steel, particularly SUS316 or the like, can, for example, be used as a material of vibrating electrode member 35 and electrically conductive member 36. Electrically conductive member 36 is inserted into opening 14 of diaphragm 11. An insulating sleeve 33 is disposed on an outer circumferential side surface of electrically conductive member 36. An O ring 15 functioning as a sealing member that seals a portion between opening 14 and an outer circumferential surface of insulating sleeve 33 is disposed on an outer circumference of insulating sleeve 33. O ring 15 seals a portion between an inner wall of opening 14 and insulating sleeve 33 in an airtight manner.

From a different perspective, in cell sorter 1 described above, electrically conductive member 36 extends from the exterior of sterilization treatment possible region 12 (non-sterilization treatment region 13) through opening 14 to sterilization treatment possible region 12. Electrically conductive member 36 is connected to vibrating electrode member 35. Vibrating electrode member 35 and electrically conductive member 36 form a vibrating electrode 30. O ring 15 functioning as a sealing member seals a portion between electrically conductive member 36 and diaphragm 11 in an airtight manner. Ultrasonic vibration generation portion 31 is disposed on the exterior of sterilization treatment possible region 12 and is connected to electrically conductive member 36. Ultrasonic vibration generation portion 31 is connected to controller 71. Ultrasonic vibration generation portion 31 may include, for example, a piezoelectric element. Controller 71 functioning as an electric charge supply portion is disposed on the exterior of sterilization treatment possible region 12 (in non-sterilization treatment region 13) and supplies an electric charge to electrically conductive member 36. Controller 71 controls ultrasonic vibration generation portion 31 and supplies an electric charge to electrically conductive member 36. The electric charge supplied to electrically conductive member 36 is supplied into chamber 21 through vibrating electrode member 35. An ultrasonic vibration applied to electrically conductive member 36 by ultrasonic vibration generation portion 31 is propagated to vibrating electrode member 35 and further is transmitted into chamber 21. That is, vibrating electrode member 35 can supply an electric charge to the sheath liquid and the sample liquid in chamber 21 and propagate an ultrasonic vibration.

Figure 4:
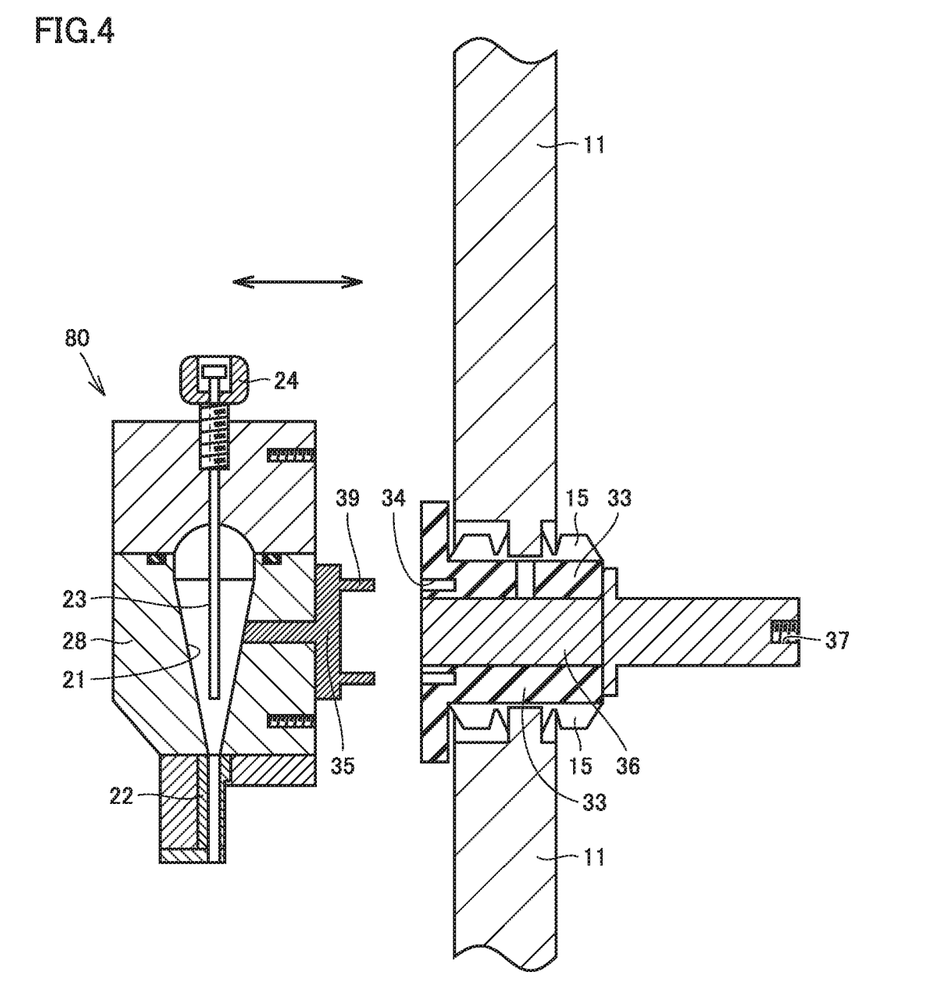
FIG. 4 is a schematic view showing a state in which a flow cell chamber unit of the treatment apparatus shown in FIG. 1 has been detached.

As shown in FIG. 4, vibrating electrode member 35 is configured to be detachable from electrically conductive member 36 as shown by an arrow in FIG. 4. From a different perspective, vibrating electrode member 35 and electrically conductive member 36 are detachably connected. Specifically, vibrating electrode member 35 has a protrusion 39. Vibrating electrode member 35 shown in FIG. 4 is provided with a plurality of protrusions 39 (in FIG. 4, two protrusions 39). At a position facing protrusion 39, a hole 34 is formed in insulating sleeve 33 surrounding electrically conductive member 36. Protrusion 39 is inserted into hole 34, and vibrating electrode member 35 is thereby connected to electrically conductive member 36. That is, flow cell chamber unit 80 can be detached from electrically conductive member 36. Protrusion 39 and hole 34 described above correspond to a positioning mechanism configured to define a connection position of vibrating electrode member 35 with respect to electrically conductive member 36. Hole 34 may be formed in electrically conductive member 36. In this case, electrically conductive member 36 and vibrating electrode member 35 can be reliably connected by a contact portion of hole 34 and protrusion 39. As the positioning mechanism, a hole may be formed in vibrating electrode member 35, and a protrusion may be formed at a position of insulating sleeve 33 or electrically conductive member 36 facing the hole, for example. In addition to the combination of protrusion 39 and hole 34 shown in FIG. 4, an arbitrary configuration that allows positioning can be used as the configuration of the positioning mechanism. A metal-plated layer (as a specific example, a nickel-plated layer) may, for example, be formed on the connection portion of vibrating electrode member 35 and electrically conductive member 36 in order to enhance the electric joining property. Alternatively, an electrically conductive seal member may be disposed on the connection portion.

(Optical Mechanism)

A window portion 18 is formed at a position of diaphragm 11 facing optical mechanism 61. Window portion 18 is made of, for example, a material that allows light emitted from optical mechanism 61 or light received by optical mechanism 61 to transmit therethrough. Optical mechanism 61 is disposed on the exterior of sterilization treatment possible region 12 (for example, in non-sterilization treatment region 13). Optical mechanism 61 is for obtaining information of the biological particles included in the liquid flow formed in flow cell chamber unit 80. Optical mechanism 61 may include, for example, a laser beam source configured to apply a laser beam to the individual cell particles arranged in line in flow cell 22 as well as an optical system such as a lens. Optical mechanism 61 may also include a light reception portion configured to detect scattered light and/or fluorescence from the cell particles irradiated with the laser beam and detect identification information of the cell particles. Optical mechanism 61 may also include an image pickup portion configured to measure an interval between droplets 51 released downward from flow cell 22. Optical mechanism 61 is connected to controller 71. Controller 71 transmits a control signal for controlling optical mechanism 61. Controller 71 may also receive the above-described identification information from the light reception portion of optical mechanism 61.

(Sorter Mechanism Portion)

Figure 1:
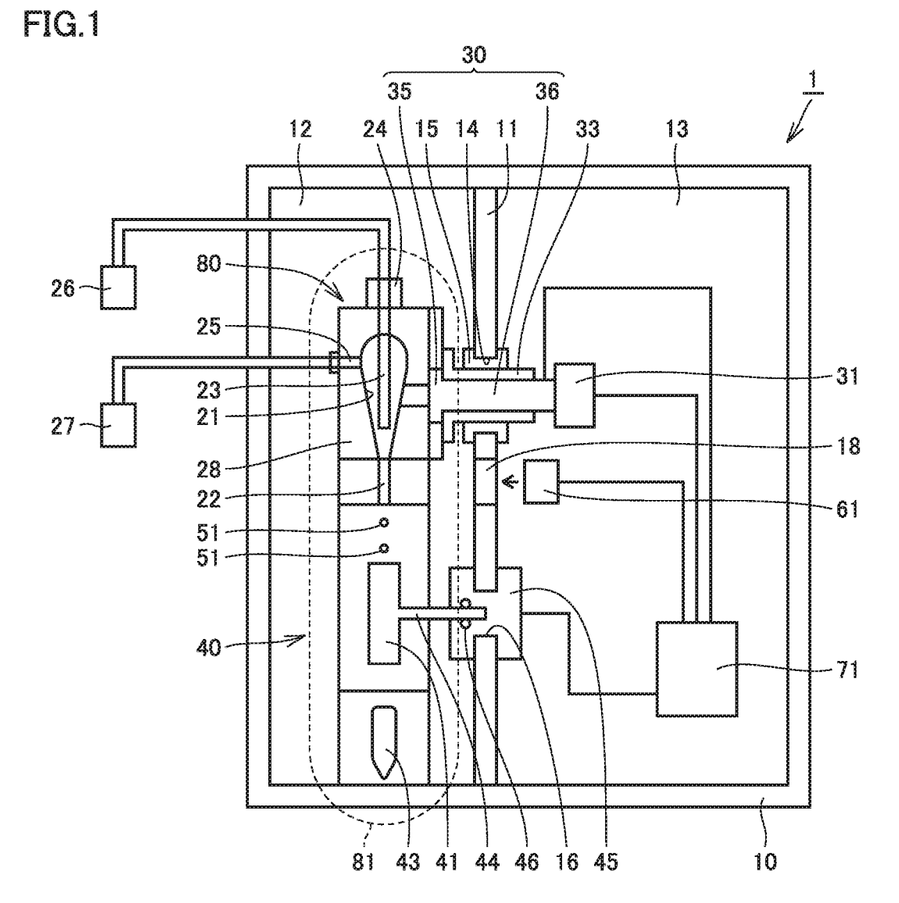
FIG. 1 is a schematic cross-sectional view of a treatment apparatus according to the present embodiment.
Figure 3:
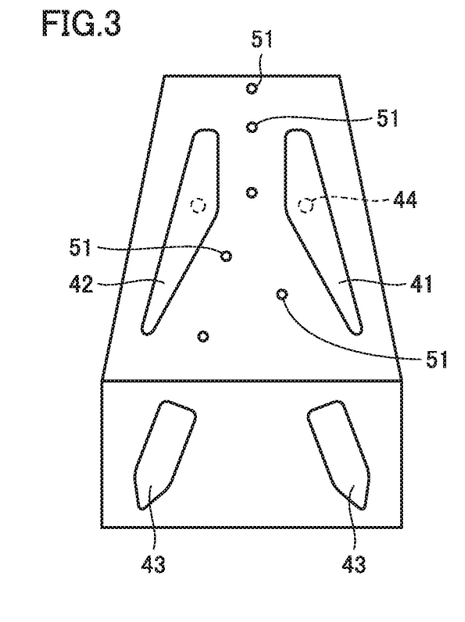
FIG. 3 is a schematic partial cross-sectional view of the treatment apparatus shown in FIG. 1.

As shown in FIGS. 1 and 3, sorter mechanism portion 40 includes a pair of deflection plates 41 and 42. Deflection plates 41 and 42 have a basically similar configuration. The configuration will be described, taking deflection plate 41 shown in FIG. 1 as a typical example. Deflection plate 41 is provided with an extending portion 44 extending toward diaphragm 11. An opening 16 is formed in a portion of diaphragm 11 facing extending portion 44. A connector 45 is fitted into opening 16 in an airtight manner. An opening into which extending portion 44 is inserted is formed in a surface of connector 45. Extending portion 44 is inserted into the opening. Inside the opening, an O ring 46 functioning as a sealing member is disposed between extending portion 44 and an inner wall of the opening. Extending portion 44 is connected to controller 71 through a wiring in non-sterilization treatment region 13. By applying a voltage to deflection plates 41 and 42, an electric field is formed between deflection plates 41 and 42. This electric field changes a direction of dropping of electrically charged droplets 51. Droplets 51 subjected to the change of direction of dropping are collected in prescribed collection member 43. The details will be described below.

<Operation of Treatment Apparatus>

In flow cell chamber unit 80, the sample liquid including the cell particles are supplied from sample liquid supply portion 24 through conduit 23 into chamber 21. At the same time, the sheath liquid is supplied from sheath liquid supply portion 25 into chamber 21. At this time, the sample liquid flows through chamber 21 such that the sample liquid is surrounded by the sheath liquid. In flow cell 22, the individual cell particles included in the sample liquid are arranged in line along a direction of extension of flow cell 22. That is, flow cell chamber unit 80 is designed such that the sheath liquid flows through flow cell 22 in a laminar flow state and the sample liquid flows through a central portion of the laminar flow.

Then, in optical mechanism 61, the identification information of the individual cell particles is detected and the distance information between droplets 51 on the exit side of flow cell 22 is obtained. An ultrasonic vibration is applied to the sample liquid and the sheath liquid in chamber 21 by vibrating electrode member 35, and the liquid flow is thereby separated into droplets on the exit side of flow cell 22. The interval between the droplets can be adjusted by adjusting the frequency and the like of the ultrasonic vibration. Based on the information obtained by optical mechanism 61, an electric charge corresponding to the identification information of the cell particles included in separated droplets 51 is applied to droplets 51 through the liquid in chamber 21 by vibrating electrode member 35.

Droplets 51 having the prescribed electric charge applied thereto are subjected to force due to the electric field between deflection plates 41 and 42, and the direction of dropping of droplets 51 is changed in accordance with the applied electric charge. As a result, the cell particles included in droplets 51 can be sorted in accordance with the identification information of the cell particles.

<Sterilization Treatment of Treatment Apparatus>

When different types of cell particles are treated in above-described cell sorter 1 functioning as the treatment apparatus, sterilization treatment of sort head 81 of cell sorter 1 is required. In this case, a sterilization gas is supplied to sterilization treatment possible region 12. Hydrogen peroxide vapor can, for example, be used as the sterilization gas. When the hydrogen peroxide vapor is used, a conventional apparatus has had such a problem that a connector portion of a wiring connected to sort head 81 is damaged (for example, rust is formed). However, in cell sorter 1 according to the present embodiment, a connector of a wiring or the like is not exposed to sterilization treatment possible region 12 in sort head 81, and thus, sterilization treatment can be performed using the above-described sterilization gas.

Furthermore, as shown in FIG. 4, flow cell chamber unit 80 is detached, and radiation is applied to flow cell chamber unit 80 for sterilization treatment. Such sterilization treatment using radiation allows reliable sterilization treatment of an interior of a small-diameter hole (for example, a hole having a diameter of approximately 50 μm to 200 μm) that is difficult to decontaminate by sterilization treatment using the sterilization gas. Flow cell chamber unit 80 subjected to sterilization treatment as described above is placed in cell sorter 1, and thus, treatment such as sorting of the cell particles in a sterile state can be performed. A plurality of flow cell chamber units 80 subjected to sterilization treatment as described above may be prepared and flow cell chamber units 80 may be replaced as appropriate. With this, the cell particles can be efficiently treated in a sterile state.

<Function and Effect of Treatment Apparatus>

By using flow cell chamber unit 80 described above, an electric charge and an ultrasonic vibration can be supplied from the portion (hereinafter also referred to as "extending portion") of vibrating electrode member 35 extending to the exterior of chamber 21 through vibrating electrode member 35 to the sheath liquid and the sample liquid in chamber 21. The extending portion of vibrating electrode member 35 is located outside chamber 21. Therefore, by using, for example, such a configuration that the extending portion is connected to electrically conductive member 36 having the fitting structure shown in FIGS. 2 and 4 and electrically conductive member 36 is pulled out to the exterior of sterilization treatment possible region 12, the connector of the wiring or the like is not exposed to sterilization treatment possible region 12 where chamber member 28 is disposed, and an electric charge and an ultrasonic vibration can be externally applied to vibrating electrode member 35. As a result, it is possible to prevent the occurrence of such a problem that the above-described connector or the like of vibrating electrode member 35 is damaged by the sterilization gas when sterilization treatment for removing contamination by the aerosol is performed on chamber member 28 itself using the sterilization gas. Thus, sterilization treatment can be performed using the sterilization gas, after the liquid flow including the biological particles (cell particles) is formed in chamber 21. As a result, contamination by the aerosol of the liquid flow can be reliably removed from chamber member 28.

Figure 2:
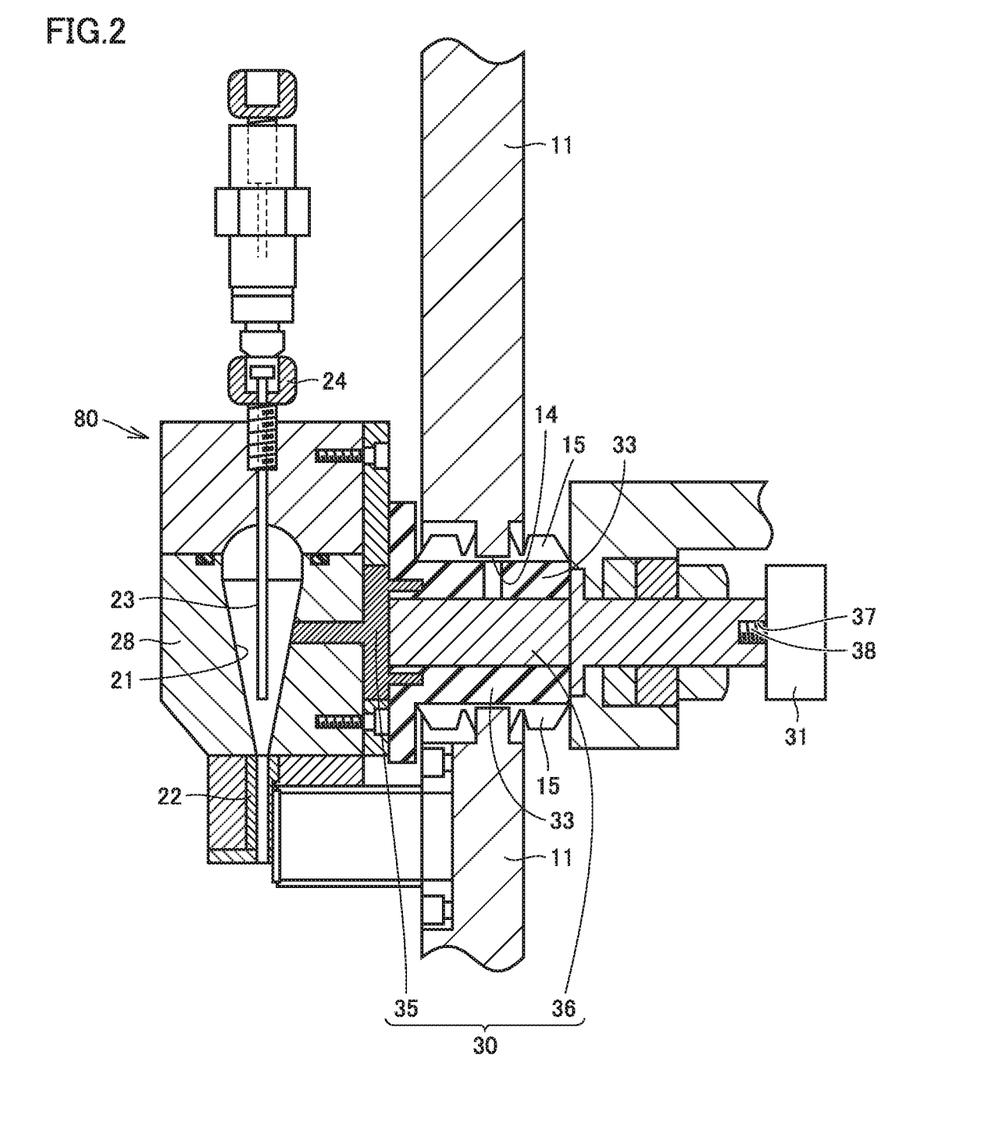
FIG. 2 is a schematic partial cross-sectional view of the treatment apparatus shown in FIG. 1.

As shown in FIGS. 1 and 2, in flow cell chamber unit 80 described above, the end face of vibrating electrode member 35 exposed to the interior of chamber 21 is disposed so as to be continuous with the portion of the inner surface of chamber 21 adjacent to the end face. In this case, the end face of vibrating electrode member 35 exposed to the interior of chamber 21 and the inner surface of chamber 21 form a smoothly continuous surface. Therefore, it is possible to reduce the possibility that a flow of the sheath liquid and the sample liquid in chamber 21 is disturbed by the end face of vibrating electrode member 35.

In above-described cell sorter 1 functioning as the treatment apparatus, above-described flow cell chamber unit 80 is disposed in sterilization treatment possible region 12. Therefore, the sterilization gas such as hydrogen peroxide vapor can be supplied into sterilization treatment possible region 12 and sterilization treatment of above-described flow cell chamber unit 80 can be reliably performed. Thus, contamination by the aerosol of the sample liquid and the like can be reliably removed in above-described flow cell chamber unit 80.

In addition, in above-described cell sorter 1, electricity can be supplied to vibrating electrode member 35 through electrically conductive member 36 and an ultrasonic vibration can be supplied to the sheath liquid and the sample liquid in chamber 21. If the connection portion of electrically conductive member 36 and the extending portion of vibrating electrode member 35 is configured in an airtight manner, the sterilization gas never comes into contact with the connection portion of vibrating electrode member 35 and electrically conductive member 36 even when the gas is supplied to sterilization treatment possible region 12 and sterilization treatment of above-described flow cell chamber unit 80 is performed using the gas. Thus, it is possible to reduce the possibility that the connection portion is damaged by the above-described gas.

In addition, as shown in FIG. 4, vibrating electrode member 35 and electrically conductive member 36 are detachably connected, and thus, flow cell chamber unit 80 is detachable from cell sorter 1. Therefore, after sterilization treatment of flow cell chamber unit 80 is performed in sterilization treatment possible region 12 using the sterilization gas (for example, hydrogen peroxide vapor), flow cell chamber unit 80 can be detached from cell sorter 1 and further sterilization treatment (for example, sterilization treatment using radiation) can be performed. Thus, the cell particles can be reliably treated in a sterile state.

In addition, as shown in FIG. 4, cell sorter 1 includes the positioning mechanism (protrusion 39 and hole 34), and thus, flow cell chamber unit 80 can be easily positioned when flow cell chamber unit 80 is attached to cell sorter 1.

In addition, in above-described cell sorter 1, optical mechanism 61 is disposed on the exterior of sterilization treatment possible region 12. Therefore, even when the sterilization gas is supplied to sterilization treatment possible region 12 and sterilization treatment of flow cell chamber unit 80 is performed, the sterilization gas never comes into contact with optical mechanism 61. Thus, it is possible to prevent the occurrence of such a problem that optical mechanism 61 is damaged by the gas.

While the embodiment of the present invention has been described above, the above-described embodiment can also be modified variously. In addition, the scope of the present invention is not limited to the above-described embodiment. The scope of the present invention is defined by the terms of the claims, and is intended to include any modifications within the scope and meaning equivalent to the terms of the claims.

INDUSTRIAL APPLICABILITY

The present invention is particularly advantageously applied to a flow cytometer or a cell sorter for treating cell particles.

REFERENCE SIGNS LIST 1 cell sorter; 10 sterilization treatment portion; 11 diaphragm; 12 sterilization treatment possible region; 13 non-sterilization treatment region; 14, 16 opening; 15, 46 O ring; 18 window portion; 21 sample mixing chamber; 22 flow cell; 23 conduit; 24 sample liquid supply portion; 25 sheath liquid supply portion; 26 sample liquid source portion; 27 sheath liquid source portion; 28 chamber member; 30 vibrating electrode; 31 ultrasonic vibration generation portion; 33 insulating sleeve; 34 hole; 35 vibrating electrode member; 36 electrically conductive member; 39 protrusion; 40 sorter mechanism portion; 41, 42 deflection plate; 43 collection member; 44 extending portion; 45 connector; 51 droplet; 61 optical mechanism; 71 controller; 80 flow cell chamber unit; 81 sort head.

The invention claimed is:
1. An apparatus for forming a liquid flow including biological particles, the apparatus comprising:
 a chamber member including a chamber and a flow cell extending from an interior to an exterior of the chamber;
 a sample liquid supply portion configured to supply a sample liquid including the biological particles into the chamber;
 a sheath liquid supply portion configured to supply a sheath liquid into the chamber; and
 a vibrating electrode member extending from the interior to the exterior of the chamber, made of an electrically conductive material, and configured to be capable of supplying an electric charge to the sheath liquid and the sample liquid in the chamber and propagating an ultrasonic vibration.

2. The apparatus according to claim 1, wherein
an end face of the vibrating electrode member exposed to the interior of the chamber is disposed so as to be continuous with a portion of an inner surface of the chamber adjacent to the end face.

3. A treatment apparatus comprising:
a sterilization treatment portion including a sterilization treatment possible region where sterilization treatment is possible; and
the apparatus as recited in claim 1, the apparatus being disposed in the sterilization treatment possible region.

4. The treatment apparatus according to claim 3, wherein
the sterilization treatment portion includes a diaphragm configured to partition an exterior of the sterilization treatment possible region and the sterilization treatment possible region,
an opening is formed in the diaphragm, and
the treatment apparatus comprises:
an electrically conductive member extending from the exterior of the sterilization treatment possible region through the opening to the sterilization treatment possible region and connected to the vibrating electrode member;
a sealing member configured to seal a portion between the electrically conductive member and the diaphragm in an airtight manner;
an ultrasonic vibration generation portion disposed on the exterior of the sterilization treatment possible region and connected to the electrically conductive member; and
an electric charge supply portion disposed on the exterior of the sterilization treatment possible region and configured to supply an electric charge to the electrically conductive member.

5. The treatment apparatus according to claim 4, wherein
the vibrating electrode member and the electrically conductive member are detachably connected.

6. The treatment apparatus according to claim 5, further comprising
a positioning mechanism configured to define a connection position of the vibrating electrode member with respect to the electrically conductive member.

7. The treatment apparatus according to claim 3, further comprising:
an optical mechanism disposed on the exterior of the sterilization treatment possible region and configured to obtain information of the biological particles included in the liquid flow formed in the apparatus.

* * * * *